(12) United States Patent
Tseng et al.

(10) Patent No.: US 10,959,624 B2
(45) Date of Patent: Mar. 30, 2021

(54) METHODS OF MONITORING FOR HEMODYNAMICALLY SIGNIFICANT HEART RHYTHM DISTURBANCES AND DEVICES FOR PRACTICING SAME

(71) Applicant: The Regents of the University of California, Oakland, CA (US)

(72) Inventors: Zian Tseng, Tiburon, CA (US); Gregory Marcus, Kentfield, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/651,924

(22) PCT Filed: Oct. 5, 2018

(86) PCT No.: PCT/US2018/054711
§ 371 (c)(1),
(2) Date: Mar. 27, 2020

(87) PCT Pub. No.: WO2019/071198
PCT Pub. Date: Apr. 11, 2019

(65) Prior Publication Data
US 2020/0305737 A1    Oct. 1, 2020

Related U.S. Application Data

(60) Provisional application No. 62/569,024, filed on Oct. 6, 2017.

(51) Int. Cl.
*A61B 5/024*    (2006.01)
*A61B 5/00*    (2006.01)
*A61B 5/0205*    (2006.01)

(52) U.S. Cl.
CPC .......... *A61B 5/02416* (2013.01); *A61B 5/002* (2013.01); *A61B 5/0205* (2013.01);
(Continued)

(58) Field of Classification Search
CPC .................................................. A62B 5/02416
See application file for complete search history.

(56) References Cited

U.S. PATENT DOCUMENTS 9,649,039 B1 *   5/2017   Brady ............... A61B 5/02427
2015/0359443 A1   12/2015   Poh
(Continued)

OTHER PUBLICATIONS

Cheriyedath (2016) "Photoplethysmography (PPG)" Medical Life Sciences, 4pgs.
(Continued)

*Primary Examiner* — Travis R Hunnings
(74) *Attorney, Agent, or Firm* — Brian E. Davy; Bozicevic, Field & Francis LLP (57) ABSTRACT

Provided are methods of monitoring for a hemodynamically significant heart rhythm disturbance. The methods include obtaining baseline photoplethysmography (PPG) data from an individual, obtaining PPG signals from the individual during a monitoring period, comparing the PPG signals obtained during the monitoring period to the baseline PPG data, and producing an output when a hemodynamically significant heart rhythm disturbance is detected. In some aspects, the heart rhythm disturbance is detected based on a threshold reduction in PPG amplitude in the PPG signals obtained during the monitoring period compared to the baseline PPG data for a selected period of time; a threshold decreased slope in the initial positive deflection in PPG signals obtained during the monitoring period compared to the baseline PPG data for a selected number of consecutive beats; or both. Also provided are computer-readable media and computing devices that find use, e.g., in practicing the methods of the present disclosure.

20 Claims, 5 Drawing Sheets

(52) U.S. Cl.
CPC ...... *A61B 5/02055* (2013.01); *A61B 5/02405* (2013.01); *A61B 5/02433* (2013.01); *A61B 5/02438* (2013.01); *A61B 5/681* (2013.01); *A61B 5/7246* (2013.01); *A61B 5/742* (2013.01); *A61B 5/7405* (2013.01); *A61B 5/747* (2013.01); *A61B 5/7455* (2013.01)

(56) References Cited

U.S. PATENT DOCUMENTS

| | | | |
|---|---|---|---|
| 2017/0071551 A1* | 3/2017 | Jain | A61B 5/0006 |
| 2019/0133516 A1* | 5/2019 | Banet | A61B 5/0537 |
| 2019/0142286 A1* | 5/2019 | Mouradian | A61B 5/0261 |
| | | | 600/480 |

OTHER PUBLICATIONS

Shan et al. (2016) "Reliable PPG-based algorithm in atrial fibrillation detection" IEEE Biomedical Circuits and Systems Conference (BioCAS), 340-343.

Shim (2008) "Development of Heart Rate Monitoring for Mobile Telemedicine using Smartphone" ICBME Proceedings, 23:1116-1119.

* cited by examiner

METHODS OF MONITORING FOR HEMODYNAMICALLY SIGNIFICANT HEART RHYTHM DISTURBANCES AND DEVICES FOR PRACTICING SAME

CROSS-REFERENCE TO RELATED APPLICATIONS

This application claims the benefit of U.S. Provisional Patent Application No. 62/569,024, filed Oct. 6, 2017, which application is incorporated herein by reference in its entirety.

INTRODUCTION

Technologies for measuring heart rate metrics include electrocardiography (ECG or EKG) and photoplethysmography (PPG). ECG involves recording the electrical activity of the heart over a period of time using electrodes placed on the skin. The electrodes detect electrical changes on the skin that arise from the electrophysiologic pattern of depolarizing and repolarizing of the heart muscle during each heartbeat. For example, in 12-lead ECG, ten electrodes are placed on the limbs and surface of the chest of a patient. The overall magnitude of the electrical potential of the heart is then measured from twelve different angles (or "leads") and is recorded over a period of time, e.g., ten or more seconds. The overall magnitude and direction of the heart's electrical depolarization is captured at each moment throughout the cardiac cycle. The non-invasive electrocardiography procedure produces a graph of voltage versus time, referred to as an electrocardiogram.

Photoplethysmography (PPG) is an optical technique that can be used to detect blood volume changes in the microvascular bed of tissue. It is often used non-invasively to make measurements at the skin surface. The PPG waveform comprises a pulsatile ("AC") physiological waveform attributed to cardiac synchronous changes in the blood volume with each heartbeat, and may be superimposed on a slowly varying ("DC") baseline with various lower frequency components attributed to respiration, sympathetic nervous system activity and thermoregulation. PPG technology has been used in a wide range of commercially available medical devices for measuring oxygen saturation, heart rate, blood pressure and cardiac output, assessing autonomic function and also detecting peripheral vascular disease.

The heart pumps blood to the periphery with each cardiac cycle. Although this pressure pulse is somewhat damped by the time it reaches the skin, it is enough to distend the arteries and arterioles in the subcutaneous tissue. The change in volume caused by the pressure pulse may be detected by illuminating the skin with the light from a light-emitting diode (LED) and then measuring the amount of light either transmitted or reflected to a photodiode. Photoplethysmography has the advantage of being a low cost, simple and portable technology which can be used in primary health care and remote clinics.

Cardiac arrest leading to sudden cardiac death (SCD) is a major cause of worldwide mortality. Early rescue (e.g., within 2-5 minutes) from lethal heart rhythms by emergency medical systems (EMS) paramedics is the most important and critical determinant of survival from otherwise fatal cardiac arrests. The large majority of cardiac arrests are unwitnessed and therefore cannot be rescued because EMS is not alerted, while many witnessed cardiac arrest victims suffer a delay to EMS alert, preventing timely rescue. By definition, a cardiac arrest manifests as a hemodynamically unstable, i.e., pulseless rhythm. The majority of these arrests are preceded by known heart rhythm disturbances with idiosyncratic characteristics.

The methods and systems disclosed herein utilize unconventional aspects of PPG signals to monitor for a hemodynamically significant heart rhythm disturbance in an individual, and optionally, provide an output (e.g., an alert) to the individual, a bystander, and/or a first responder to increase the likelihood of early rescue from, e.g., a lethal heart rhythm disturbance.

SUMMARY

Provided are methods of monitoring for a hemodynamically significant heart rhythm disturbance. The methods include obtaining baseline photoplethysmography (PPG) data from an individual, obtaining PPG signals from the individual during a monitoring period, comparing the PPG signals obtained during the monitoring period to the baseline PPG data, and producing an output when a hemodynamically significant heart rhythm disturbance is detected. In some aspects, the heart rhythm disturbance is detected based on a threshold reduction in PPG amplitude in the PPG signals obtained during the monitoring period compared to the baseline PPG data for a selected period of time; a threshold decreased slope in the initial positive deflection in PPG signals obtained during the monitoring period compared to the baseline PPG data for a selected number of consecutive beats; or both. Also provided are computer-readable media and computing devices that find use, e.g., in practicing the methods of the present disclosure.

DETAILED DESCRIPTION

Provided are methods of monitoring for a hemodynamically significant heart rhythm disturbance. The methods include obtaining baseline photoplethysmography (PPG) data from an individual, obtaining PPG signals from the individual during a monitoring period, comparing the PPG signals obtained during the monitoring period to the baseline PPG data, and producing an output when a hemodynamically significant heart rhythm disturbance is detected. In some aspects, the heart rhythm disturbance is detected based on a threshold reduction in PPG amplitude in the PPG signals obtained during the monitoring period compared to the baseline PPG data for a selected period of time; a threshold decreased slope in the initial positive deflection in PPG signals obtained during the monitoring period compared to the baseline PPG data for a selected number of consecutive beats; or both. Also provided are computer-readable media and computing devices that find use, e.g., in practicing the methods of the present disclosure.

Before the methods and systems of the present disclosure are described in greater detail, it is to be understood that the methods and systems are not limited to particular embodiments described, as such may, of course, vary. It is also to be understood that the terminology used herein is for the purpose of describing particular embodiments only, and is not intended to be limiting, since the scope of the methods and systems will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods and systems. The upper and lower limits of these smaller ranges may independently be included in the smaller ranges and are also encompassed within the methods and systems, subject to any specifically excluded limit in the stated range. Where the stated range includes one or both of the limits, ranges excluding either or both of those included limits are also included in the methods and systems.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods and systems belong. Although any methods and systems similar or equivalent to those described herein can also be used in the practice or testing of the methods and systems, representative illustrative methods and systems are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods and systems are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods and systems, which are, for clarity, described in the context of separate embodiments, may also be provided in combination in a single embodiment. Conversely, various features of the methods and systems, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods and systems and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, the present disclosure provides methods of monitoring for a hemodynamically significant heart rhythm disturbance in an individual. The methods utilize unconventional aspects of photoplethysmography (PPG) signals to monitor for a hemodynamically significant heart rhythm disturbance in an individual, and optionally, provide an output (e.g., which may include an alert) to the individual, a bystander, and/or a first responder to increase the likelihood of early rescue from, e.g., a lethal heart rhythm disturbance.

In some embodiments, the individual does not have a history of experiencing a hemodynamically significant heart rhythm disturbance. In other embodiments, the individual has a history of experiencing a hemodynamically significant heart rhythm disturbance. Individuals of interest include humans, pets (e.g., dogs, cats, etc.), horses, and the like. In certain aspects, the individual is a human.

In some embodiments, a method of the present disclosure includes obtaining baseline photoplethysmography (PPG) data from an individual (e.g., during normal sinus rhythm), obtaining PPG signals from the individual during a monitoring period, comparing the PPG signals obtained during the monitoring period to the baseline PPG data, and producing an output when a hemodynamically significant heart rhythm disturbance is detected.

According to the subject methods, the baseline PPG data is obtained from the individual (e.g., during normal sinus rhythm) for a period of time sufficient to obtain such baseline data. For example, the baseline PPG data may be obtained by obtaining PPG signals from the individual (e.g., during normal sinus rhythm) for a matter of seconds, minutes, hours, days or weeks. In some embodiments, PPG signals are obtained for from 5 seconds to 2 weeks to obtain the baseline PPG data. In certain aspects, PPG signals are obtained for 5 seconds or more, 10 seconds or more, 30 seconds or more, 1 minute or more, 2 minutes or more, 5 minutes or more, 30 minutes or more, 60 minutes or more, 12 hours or more, 24 hours or more, 2 days or more, 3 days or more, 4 days or more, 5 days or more, 6 days or more, 7 days or more, or 2 weeks or more, to obtain the baseline PPG data. In some embodiments, the baseline PPG data may be obtained by obtaining PPG signals from the individual (e.g., during normal sinus rhythm) for 2 weeks or less, for 7 days or less, for 6 days or less, for 5 days or less, for 4 days or less, for 3 days or less, for 2 days or less, for 24 hours or less, for 12 hours or less, for 60 minutes or less, for 30 minutes or less, for 5 minutes or less, for 2 minutes or less, for 1 minute or less, for 30 seconds or less, for 10 seconds or less, or for 5 seconds or less.

The subject methods may include obtaining the baseline PPG data from the individual a single time. In other aspects, the baseline PPG data is updated continuously or at a selected interval, e.g., to assure ongoing accuracy for a given individual. In some embodiments, the baseline PPG data is updated at a selected interval of at least every minute, 2 minutes, 5 minutes, 10 minutes, 60 minutes, 12 hours, 1 day, 2 days, 3 days, 4 days, 5 days, 6 days, 7 days, 10 days, or at least every 2 weeks.

As summarized above, the methods of the present disclosure include obtaining PPG signals from the individual during a monitoring period. The monitoring period is a period subsequent to a period during which the baseline PPG data is obtained. In certain aspects, the subject methods include alternating between a monitoring period and a period during which baseline PPG data is obtained and/or updated. In some embodiments, a monitoring period is 5 seconds or more, 10 seconds or more, 30 seconds or more, 1 minute or more, 2 minutes or more, 5 minutes or more, 30 minutes or more, 60 minutes or more, 12 hours or more, 24 hours or more, 2 days or more, 3 days or more, 4 days or more, 5 days or more, 6 days or more, 7 days or more, or 2 weeks or more. In certain aspects, a monitoring period is 2 weeks or less, 7 days or less, 6 days or less, 5 days or less, 4 days or less, 3 days or less, 2 days or less, 24 hours or less, 12 hours or less, 60 minutes or less, 30 minutes or less, 5 minutes or less, 2 minutes or less, 1 minute or less, 30 seconds or less, 10 seconds or less, or 5 seconds or less.

Figure 1:
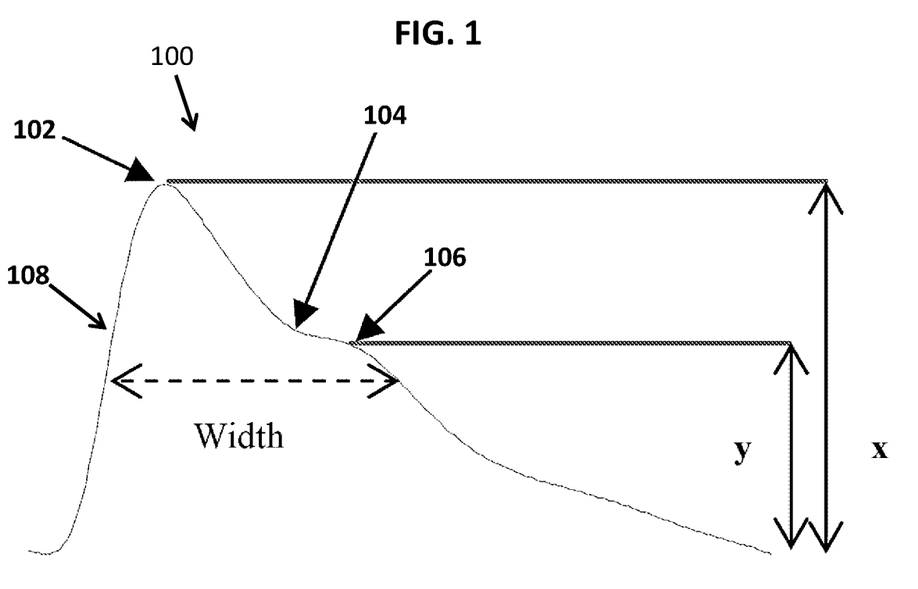
FIG. 1 shows a typical PPG waveform and its characteristic parameters.

The subject methods include comparing the PPG signals obtained during the monitoring period to the baseline PPG data. The comparison may be between any useful parameters of the PPG signals or derivatives thereof (e.g., resulting from signal processing) obtained during the monitoring period and those in the baseline PPG data. In certain aspects, the comparison involves comparing one or more PPG waveforms of the PPG data obtained during the monitoring period to a "template" PPG waveform arrived at from the baseline PPG data. Each cardiac cycle sends a pressure wave through the cardiovascular system. This pressure wave causes the blood vessels to expand and contract, which gives the PPG a characteristic waveform. A typical PPG waveform, including its characteristic parameters, is shown in FIG. 1. As shown, PPG waveform 100 includes systolic peak 102, dicrotic notch 104 (usually seen in the catacrotic phase of individuals with healthy compliant arteries), and diastolic peak 106. The waveform includes a systolic peak amplitude (designated "x" in FIG. 1) and a diastolic peak amplitude (designated "y" in FIG. 1). Details regarding the PPG waveform and PPG traces involving multiple consecutive PPG waveforms are provided, e.g., in Elgendi, M. (2012) *Current Cardiology Reviews* 8:14-25.

Also shown in FIG. 1 is initial positive deflection 108. The initial positive deflection has a slope determined by change in amplitude over time. A "decreased" slope of the initial positive deflection means that—compared to the slope of the initial positive deflection in the baseline PPG data—the slope is "flatter" and corresponds to a slower increase in amplitude over time.

Figure 2:
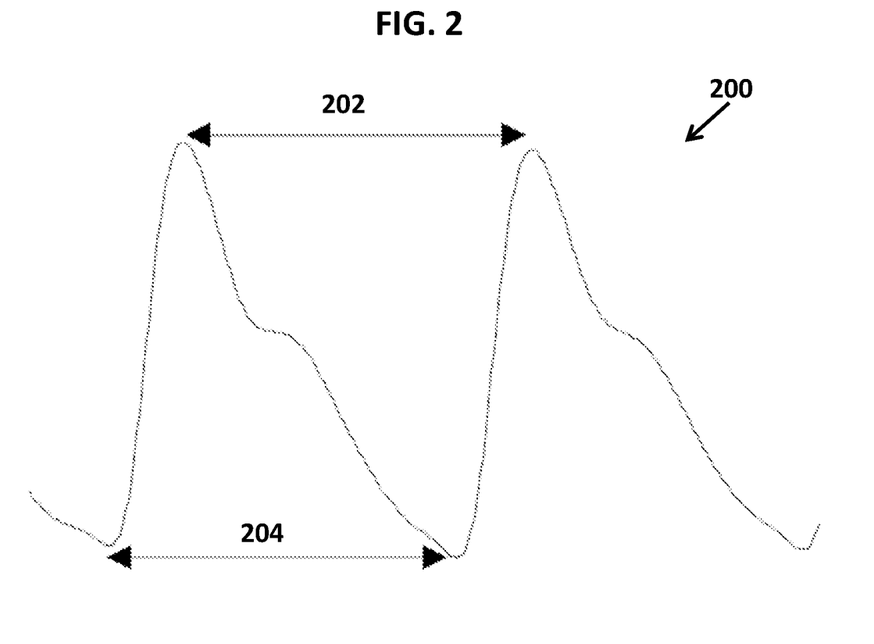
FIG. 2 shows a PPG trace including two consecutive PPG waveforms and certain parameters thereof.

In some embodiments, comparing the PPG signals obtained during the monitoring period to the baseline PPG data includes comparing one or more parameters relating to two or more consecutive PPG waveforms. A PPG trace including two consecutive typical PPG waveforms is shown in FIG. 2. Shown in FIG. 2 are two parameters of such traces, namely peak-to-peak interval 202 and pulse interval 204. In certain aspects, one or both of peak-to-peak interval and pulse interval from PPG signals obtained during the monitoring period and the baseline PPG data are compared.

As summarized above, the methods of the present disclosure include producing an output when a hemodynamically significant heart rhythm disturbance is detected. By "hemodynamically significant heart rhythm disturbance" is meant a heart rhythm disturbance associated with insufficient blood pressure that would result in symptoms in the individual, including presyncope, syncope, chest pain, altered mental status, insufficient blood flow to a bodily organ, cardiac arrest, death, or any combinations thereof. In some embodiments, the hemodynamically significant heart rhythm disturbance is selected from atrial fibrillation (AF), ventricular tachycardia (VT), ventricular fibrillation (VF), bradycardia, asystole, and any combination thereof. In certain aspects, the hemodynamically significant heart rhythm disturbance is selected from ventricular tachycardia (VT), ventricular fibrillation (VF), bradycardia, asystole, and any combination thereof.

In some embodiments, detecting a hemodynamically significant heart rhythm disturbance includes detecting a threshold reduction in PPG amplitude in the PPG signals obtained during the monitoring period compared to the baseline PPG data for a selected period of time. In certain aspects, the PPG amplitude is the systolic peak amplitude (designated "x" in FIG. 1). In other aspects, the PPG amplitude is the diastolic peak amplitude (designated "y" in FIG. 1). In still other aspects, the PPG amplitude is an amplitude measure involving both the systolic and diastolic peak amplitudes. For example, the PPG amplitude may be an amplitude arrived at using an equation in which both the systolic and diastolic peak amplitudes are variables.

In certain aspects, the threshold reduction in PPG amplitude for detecting a hemodynamically significant heart rhythm disturbance is 1% or greater, 5% or greater, 10% or greater, 15% or greater, 20% or greater, 25% or greater, 30% or greater, 35% or greater, 40% or greater, 45% or greater, 50% or greater, 55% or greater, 60% or greater, 65% or greater, 70% or greater, 75% or greater, or 80% or greater. As set forth above, for detecting a hemodynamically significant heart rhythm disturbance, the threshold reduction in PPG amplitude is for a selected period of time. In some embodiments, the selected period of time is 1 or more seconds, 2 or more seconds, 3 or more seconds, 4 or more seconds, 5 or more seconds, 6 or more seconds, 7 or more seconds, 8 or more seconds, 9 or more seconds, 10 or more seconds, 15 or more seconds, 20 or more seconds, 25 or more seconds, 30 or more seconds, 35 or more seconds, 40 or more seconds, 45 or more seconds, 50 or more seconds, 55 or more seconds, 60 or more seconds, 70 or more seconds, 80 or more seconds, 90 or more seconds, 100 or more seconds, or 2 minutes or more. In certain aspects, the selected period of time is 2 minutes or less, 100 seconds or less, 90 seconds or less, 80 seconds or less, 70 seconds or less, 60 seconds or less, 55 seconds or less, 50 seconds or less, 45 seconds or less, 40 seconds or less, 35 seconds or less, 30 seconds or less, 25 seconds or less, 20 seconds or less, 15 seconds or less, 10 seconds or less, 9 seconds or less, 8 seconds or less, 7 seconds or less, 6 seconds or less, 5 seconds or less, 4 seconds or less, 3 seconds or less, 2 seconds or less, or 1 second or less.

In some embodiments, detecting a hemodynamically significant heart rhythm disturbance includes detecting a threshold decreased slope in the initial positive deflection in PPG signals obtained during the monitoring period compared to the baseline PPG data for a selected number of consecutive beats. The initial positive deflection is shown in FIG. 1 as feature 108. As described above, the initial positive deflection has a slope determined by change in amplitude over time. A "decreased" slope of the initial positive deflection means that—compared to the slope of the initial positive deflection in the baseline PPG data—the slope is "flatter" and corresponds to a slower increase in amplitude over time.

In certain aspects, the threshold decreased slope in the initial positive deflection is 1% or greater, 2.5% or greater, 5% or greater, 7.5% or greater, 10% or greater, 15% or greater, 20% or greater, 25% or greater, 30% or greater, 35% or greater, 40% or greater, 45% or greater, 50% or greater, 55% or greater, 60% or greater, 65% or greater, 70% or greater, 75% or greater, 80% or greater, 85% or greater, 90% or greater, or 100% or greater. In some embodiments, the threshold decreased slope in the initial positive deflection is 100% or less, 95% or less, 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 7.5% or less, 5% or less, 2.5% or less, or 1% or less. In certain aspects, the selected number of beats is 1 beat, 2 or more consecutive beats, 3 or more consecutive beats, 4 or more consecutive beats, 5 or more consecutive beats, 6 or more consecutive beats, 7 or more consecutive beats, 8 or more consecutive beats, 9 or more consecutive beats, 10 or more consecutive beats, 11 or more consecutive beats, 12 or more consecutive beats, 13 or more consecutive beats, 14 or more consecutive beats, 15 or more consecutive beats, 16 or more consecutive beats, 17 or more consecutive beats, 18 or more consecutive beats, 19 or more consecutive beats, 20 or more consecutive beats, 25 or more consecutive beats, 30 or more consecutive beats, 35 or more consecutive beats, 40 or more consecutive beats, 45 or more consecutive beats, 50 or more consecutive beats, 75 or more consecutive beats, or 100 or more consecutive beats. In some embodiments, the selected number of beats is 100 or more fewer beats, 75 or fewer beats, 50 or fewer beats, 45 or fewer beats, 40 or fewer beats, 35 or fewer beats, 30 or fewer beats, 25 or fewer beats, 20 or fewer beats, 19 or fewer beats, 18 or fewer beats, 17 or fewer beats, 16 or fewer beats, 15 or fewer beats, 14 or fewer beats, 13 or fewer beats, 12 or fewer beats, 11 or fewer beats, 10 or fewer beats, 9 or fewer beats, 8 or fewer beats, 7 or fewer beats, 6 or fewer beats, 5 or fewer beats, 4 or fewer beats, 3 or fewer beats, 2 beats, or 1 beat.

In some embodiments, detecting a hemodynamically significant heart rhythm disturbance includes: detecting a threshold reduction in PPG amplitude in the PPG signals obtained during the monitoring period compared to the baseline PPG data for a selected period of time (e.g., any of the threshold reductions combined with any of the selected periods of time as described hereinabove); and detecting a threshold decreased slope in the initial positive deflection in PPG signals obtained during the monitoring period compared to the baseline PPG data for a selected number of consecutive beats (e.g., any of the threshold decreased slopes combined with any of the number of consecutive beats as described hereinabove).

Detecting a hemodynamically significant heart rhythm disturbance may be based on parameters in addition to the threshold reduction in PPG amplitude and/or threshold decreased slope in the initial positive deflection in PPG signals. For example, in some embodiments, detecting a hemodynamically significant heart rhythm disturbance further includes photoplethysmographically detecting a hemodynamically significant heart rate for a selected period of time. In certain aspects, the hemodynamically significant heart rate is 50 beats per minute (bpm) or slower, 45 bpm or slower, 40 bpm or slower, 35 bpm or slower, 30 bpm or slower, 25 bpm or slower, 20 bpm or slower, 15 bpm or slower, 10 bpm or slower, or 5 bpm or slower. In some embodiments, the hemodynamically significant heart rate is 220 bpm minus the age in years of the individual.

In certain aspects, the selected period of time for detecting a hemodynamically significant heart rhythm disturbance is 1 or more seconds, 2 or more seconds, 3 or more seconds, 4 or more seconds, 5 or more seconds, 6 or more seconds, 7 or more seconds, 8 or more seconds, 9 or more seconds, 10 or more seconds, 15 or more seconds, 20 or more seconds, 25 or more seconds, 30 or more seconds, 35 or more seconds, 40 or more seconds, 45 or more seconds, 50 or more seconds, 55 or more seconds, 60 or more seconds, 70 or more seconds, 80 or more seconds, 90 or more seconds, 100 or more seconds, or 2 minutes or more. In certain aspects, the selected period of time for detecting a hemodynamically significant heart rhythm disturbance is 2 minutes or less, 100 seconds or less, 90 seconds or less, 80 seconds or less, 70 seconds or less, 60 seconds or less, 55 seconds or less, 50 seconds or less, 45 seconds or less, 40 seconds or less, 35 seconds or less, 30 seconds or less, 25 seconds or less, 20 seconds or less, 15 seconds or less, 10 seconds or less, 9 seconds or less, 8 seconds or less, 7 seconds or less, 6 seconds or less, 5 seconds or less, 4 seconds or less, 3 seconds or less, 2 seconds or less, or 1 second or less.

A threshold reduction or absence of movement of the individual is a further parameter which may be utilized according to the subject methods for detecting and/or confirming a hemodynamically significant heart rhythm disturbance in addition to the threshold reduction in PPG amplitude and/or threshold decreased slope in the initial positive deflection in PPG signals.

A threshold reduction in body temperature of the individual is a further parameter which may be utilized according to the subject methods for detecting and/or confirming a hemodynamically significant heart rhythm disturbance in addition to the threshold reduction in PPG amplitude and/or threshold decreased slope in the initial positive deflection in PPG signals.

As summarized above, when a hemodynamically significant heart rhythm disturbance is detected, the subject methods include producing an output. In certain aspects, producing an output includes producing an alert to the individual, a bystander, or both, that a hemodynamically significant heart rhythm disturbance has been detected. The alert may be selected from a visual alert, an auditory alert, a vibratory alert, and any combination thereof. In some embodiments, the alert includes an auditory alert. The auditory alert may include one or more "beeps", a voice alert, etc., and any combinations thereof.

When the methods include producing an alert to the individual, a bystander, or both, producing the alert may include requesting a response from the individual, the bystander, or both. In certain aspects, the methods include deactivating the alert when the individual, the bystander, or both, responds to the alert. For example, when a hemodynamically significant rhythm disturbance, an alert may sound, enabling the individual to deactivate the alert. This allows the baseline PPG data to be trainable. In some embodiments, the alert is a speaking voice that can alert a bystander that the user may require help, an automated external defibrillator (AED), or a call to 911. The speaking voice may include a standard message, and alternatively or additionally, may be customizable. For example, the alert to a bystander can occur on a timer only if the individual does not deactivate the alert manually after a pre-selected period of time.

The alert-response aspects encompassed by the methods of the present disclosure enable programmability of the threshold reduction in PPG amplitude in the PPG signals obtained during the monitoring period, the threshold decreased slope in the initial positive deflection in PPG signals, or both. For example, if a given reduction in the PPG amplitude results in an alert that is manually suspended by the individual on one or two or more consecutive occasions (e.g., three consecutive occasions), the threshold reduction in PPG amplitude may be increased by a particular percentage (e.g., increased by 5%, 10%, or the like). Similarly, the selected period of time for the threshold reduction in PPG amplitude constituting a hemodynamically significant rhythm disturbance may also be programmable. For example, if a selected period of time for the threshold reduction in PPG amplitude results in an alarm that is manually suspended by a user on one or two or more consecutive occasions (e.g., three consecutive occasions), the methods may include increasing the selected period of time (e.g., by one or more seconds, 2 or more seconds, 5 or more seconds, or 10 or more seconds, or the like).

Also by way of example regarding the optional programmability aspects of the subject methods, if a given threshold decreased slope in the initial positive deflection results in an alert that is manually suspended by the individual on one or two or more consecutive occasions (e.g., three consecutive occasions), the threshold decreased slope may be increased by a particular percentage (e.g., increased by 5%, 10%, or the like). Similarly, the selected number of consecutive beats for the threshold decreased slope in the initial positive deflection may also be programmable. For example, if a selected number of consecutive beats for the threshold decreased slope in the initial positive deflection results in an alert that is manually suspended by the individual on one or two or more consecutive occasions (e.g., three consecutive occasions), the selected number of consecutive beats may be increased (e.g., increased by 1 beat, 5 beats, 10 beats, or the like).

In some embodiments, the methods may include a training period for the individual before "arming" the device used to monitoring for a hemodynamically significant heart rhythm disturbance in an individual. For example, the individual may wear the device for a selected period of time (1 or more days, a week, or the like) without any alarm turned "on." During that selected period of time, the baseline PPG amplitude and/or baseline slope in the initial positive deflection, as well as a suitable period of time and selected number of consecutive beats, can be determined. The subject methods may include selecting the threshold reduction in PPG amplitude, the selected period of time for the threshold reduction, the threshold decreased slope in the initial positive deflection, and/or the number of consecutive beats for the threshold decreased slope in the initial positive deflection, based on the training period. A heart rate deemed hemodynamically significant, e.g., due to bradycardia, tachycardia, or the like, may be trained as detailed above, including using manual deactivation of alerts and/or a training period before the device is "armed."

The optional training period may also be based on physical activity of the individual as detected by, e.g., an accelerometer present in the device used for monitoring for a hemodynamically significant heart rhythm disturbance. For example, if there is no evidence of motion consistent with walking or running, a parameter deemed to meet the threshold criteria for a hemodynamically significant heart rhythm disturbance can be adjusted and/or the period of time, number of consecutive beats, or the like, required to deem a hemodynamically significant heart rhythm disturbance can be adjusted.

In certain aspects, producing an output comprises producing an alert to a first responder.

In some embodiments, an alert to a first responder is produced only in the absence of a response from the individual to an alert to the individual. For example, an alert to a first responder may be produced only when the individual does not dismiss or suspend an alert to the individual. A first responder who may be alerted according to the subject methods includes an emergency medical service (EMS), the police, a fire department, and any combination thereof.

An alert to a first responder may be transmitted in a variety of ways. In some embodiments, the alert is transmitted to a first responder via a wireless network. Wireless networks of interest include, but are not limited to, those that employ a network standard selected from GSM, CDMA, LTE, IMS, Universal Mobile Telecommunication System (UMTS), 3G, 4G, 5G, 6G and upper, RFID, and so forth. In certain aspects, the alert to a first responder is transmitted directly from the device carrying out the heart rhythm disturbance monitoring, e.g., a wearable device (e.g., a wrist-worn device, such as a smartwatch, fitness tracker, or the like). In other aspects, such a device is connected to a second device (e.g., a smartphone, tablet computer, or the like) and the alert to a first responder is transmitted from the second device. The device carrying out the heart rhythm disturbance monitoring and the second device may be communicatively coupled by any convenient approach, including wirelessly via a Wi-Fi network, Bluetooth network, or the like.

Producing an alert to a first responder may include providing the location of the individual to the first responder, e.g., via GPS, mobile network (e.g., cellular network) triangulation, WiFi, and/or other suitable location-determining functionality present on the device carrying out the heart rhythm disturbance monitoring and/or a second device communicatively coupled thereto.

The methods of the present disclosure may be carried out using any convenient device having a PPG sensor, including any of the computing devices of the present disclosure. In some embodiments, the device is a wearable device. Such a device is sized and configured to be worn on a specific portion of the individual's body (e.g., forehead, ear, upper arm, wrist, leg, torso, or the like) while retaining the ability of the individual to move from place to place. In some embodiments, the wearable device is a wrist-wearable device, such as a smartwatch, fitness tracker, or the like.

Aspects of the methods of the present disclosure include approaches for prolonging the battery life of the device employed for carrying out the heart rhythm disturbance monitoring. In some embodiments, the device can loop at recurring intervals (e.g., every 5 seconds). If a beat is detected that meets the threshold criteria for the decreased PPG amplitude and/or decreased slope in the initial positive deflection (e.g., that is either 60% lower in amplitude or 60% slower in initial slope) or at a heart rate meeting pre-specified criteria, the device will then record continuously (or at, e.g., >300 Hertz) for a selected period of time, e.g., 5 seconds or other selected period of time.

Aspects of the methods of the present disclosure include approaches for avoiding unnecessary alarms or false positives when the device is removed. For example, the individual can press a button (a physical button or "button" on a touchscreen) to deactivate the monitoring. In the case of a wearable device (e.g., smartwatch), an accelerometer, gyroscope, and/or the like, of the wearable device can be trained to recognize the motion when the device is removed and automatically deactivate the monitoring when the device is removed. Similarly, an accelerometer, gyroscope, and/or the like, of the wearable device can be trained to recognize the motion when the device is operably coupled to the individual and automatically turn on when the device is operably coupled to the individual. For devices having a temperature sensor, a change from the baseline wearer temperature can also be used to determine if device is removed. In some embodiments, the device is a smartwatch, and a smartwatch band that automatically turns the monitoring off when unfastened and automatically turns the monitoring on when fastened may be employed. In certain aspects, the monitoring is only turned on when the device recognizes that it is operably coupled (e.g., with respect to obtaining PPG signals) to the skin of the individual.

Computer-Readable Media and Computing Devices

As summarized above, the present disclosure provides computer-readable media and computing devices. In certain aspects, the subject computer-readable media and computing devices find use in carrying out the methods of the present disclosure, e.g., any of the methods described elsewhere herein.

In some embodiments provided is a non-transitory computer-readable medium storing instructions that, when executed by a computing device, cause the computing device to: obtain baseline photoplethysmography (PPG) data from an individual (e.g., during normal sinus rhythm); obtain PPG signals from the individual during a monitoring period; compare the PPG signals obtained during the monitoring period to the baseline PPG data; and produce an output when a hemodynamically significant heart rhythm disturbance is detected. Detecting a hemodynamically significant heart rhythm disturbance includes: detecting a threshold reduction in PPG amplitude in the PPG signals obtained during the monitoring period compared to the baseline PPG data for a selected period of time; detecting a threshold decreased slope in the initial positive deflection in PPG signals obtained during the monitoring period compared to the baseline PPG data for a selected number of consecutive beats; or both. The non-transitory computer-readable medium may include instructions for carrying out the methods of the present disclosure, including any of the methods described elsewhere herein.

In certain embodiments, instructions in accordance with the methods and computing devices described herein can be coded onto a non-transitory computer-readable medium in the form of "programming", where the term "computer-readable medium" as used herein refers to any storage or transmission medium that participates in providing instructions and/or data to a computing device for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to a device carrying out the hemodynamically significant heart rhythm disturbance monitoring. A file containing information can be "stored" on computer readable medium, where "storing" means recording information such that it is accessible and retrievable at a later date by a computer. In some embodiments, the non-transitory computer-readable medium is (or is included in) a remote server, and the instructions are downloadable from the server to a computing device. The computing device to which the instructions are downloaded may be a device that carries out the hemodynamically significant heart rhythm disturbance monitoring, or a second device (e.g., smartphone, tablet computer, or the like) communicatively coupled to the monitoring device.

The instructions may be in the form of programming that is written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as many others.

Also provided are computing devices for monitoring for a hemodynamically significant heart rhythm disturbance in an individual. Such devices include a PPG sensor, a processing unit, and a non-transitory computer-readable medium including instructions that, when executed by the computing device, cause the computing device to: using the PPG sensor, obtain baseline photoplethysmography (PPG) data from an individual during normal sinus rhythm; using the PPG sensor, obtain PPG signals from the individual during a monitoring period; compare the PPG signals obtained during the monitoring period to the baseline PPG data; and produce an output when a hemodynamically significant heart rhythm disturbance is detected. Detecting a hemodynamically significant heart rhythm disturbance includes detecting a threshold reduction in PPG amplitude in the PPG signals obtained during the monitoring period compared to the baseline PPG data for a selected period of time; detecting a threshold decreased slope in the initial positive deflection in PPG signals obtained during the monitoring period compared to the baseline PPG data for a selected number of consecutive beats; or both.

In some embodiments, the computing device is adapted to carry out the methods of the present disclosure, including any of the methods described elsewhere herein.

Figure 3:
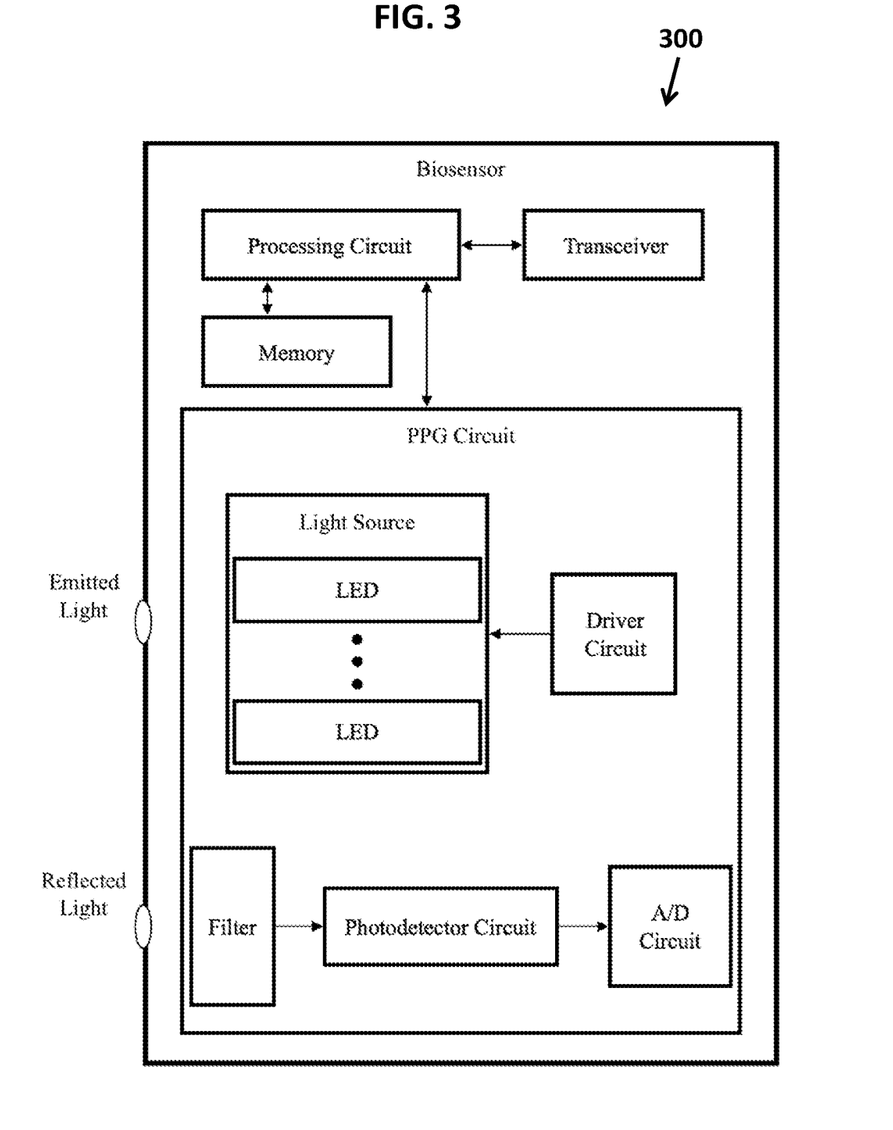
FIG. 3 schematically illustrates a computing device according to one embodiment.

A computing device according to certain aspects of the present disclosure is schematically illustrated in FIG. 3. As shown, computing device 300 (e.g., a wearable computing device, such as a smartwatch) includes a PPG circuit that includes a light source which may have a plurality of light sources (such as the 2 LEDs indicated), configured to emit light through at least one aperture. The PPG circuit is configured to direct the emitted light at an outer or epidermal layer of skin tissue of an individual. The light source is configured to emit light in one or more spectrums, including infrared (IR) light, ultraviolet (UV) light, near IR light or visible light, in response to a driver circuit. For example, computing device 300 may include a first LED that emits visible light and a second LED that emits infrared light, a third LED that emits UV light, etc. The light source may include tunable LEDs or lasers operable to emit light over one or more frequencies or ranges of frequencies or spectrums in response to the driver circuit. The driver circuit is configured to control one or more LEDs to generate light at one or more frequencies for predetermined periods of time. The driver circuit may control the LEDs to operate concurrently or progressively. The driver circuit may control a power level, emission period and frequency of emission of the LEDs. Computing device 300 is thus configured to emit one or more frequencies of light in one or more spectrums that is directed at the surface or epidermal layer of the skin tissue of an individual. The PPG circuit further includes one or more photodetector circuits. For example, a photodetector circuit may be configured to detect visible light and a second photodetector circuit may be configured to detect IR light. A photodetector circuit may include a filter to filter ambient light and/or scattered light. For example, in some embodiments, only light received at an approximately perpendicular angle to the skin surface of the individual is desired to pass through the filter. A photodetector circuit may be coupled to an A/D circuit. The A/D circuit may also include an amplifier and other components useful to generate a spectral response. Light detected by two or more photodetectors may added and amplified to generate a single spectral response. Also shown in FIG. 3 is a processing circuit (or processing unit), memory and transceiver.

In certain aspects, the computing device is a wearable device. Wearable devices are sized and configured to be worn on a specific portion of the individual's body (e.g., forehead, ear, upper arm, wrist, leg, torso, or the like) while retaining the ability of the individual to move from place to place. In some embodiments, the wearable device is a wrist-wearable device, such as a smartwatch, fitness tracker, or the like. When the wearable device is a wrist-wearable device, the device may be a smartwatch and/or fitness tracker such as an Apple Watch developed and sold by Apple, Inc. (Cupertino, Calif.), a smartwatch developed and sold by Samsung, Inc. (e.g., a Gear® smartwatch), an Android wear-based smartwatch (e.g., an Android wear-based smartwatch by LG Electronics, Inc.), or any other smartwatch and/or fitness tracker having PPG sensing functionality.

Figure 4:
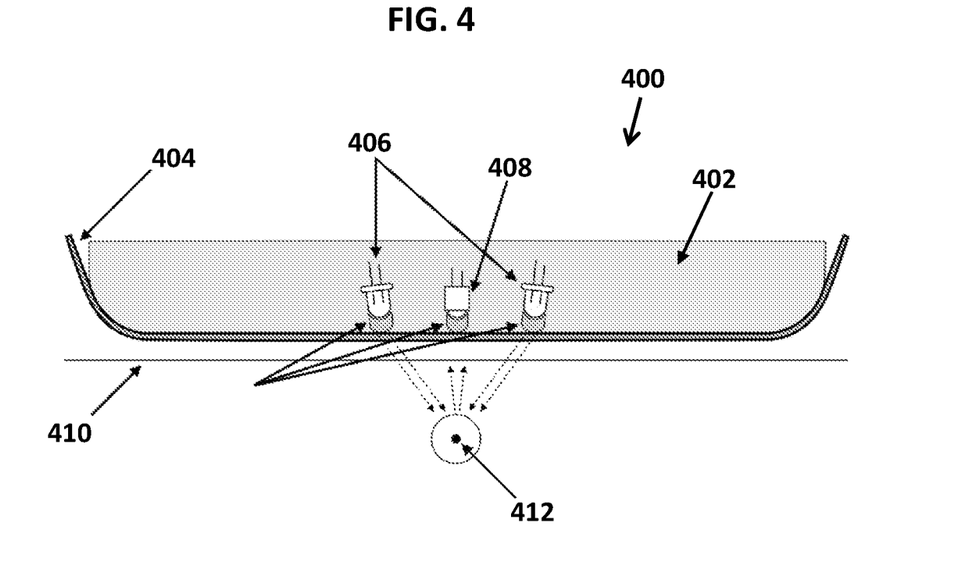
FIG. 4 schematically illustrates a computing device according to one embodiment.

A portion of an example wearable device operably coupled to the skin of an individual is schematically illustrated in FIG. 4. As shown, wearable device 400 (e.g., a smartwatch or the like) includes a body that includes light-blocking material 402 and protective transparent layer 404. Wearable device 400 further includes LEDs 406 and photodetector 408. As shown, wearable device is positioned on skin surface 410 of an individual and the LEDs and photodetector are adapted to obtain PPG signals in one or more blood vessels (e.g., artery 412) of the individual.

Utility

The methods, computer-readable media and computing devices of the present disclosure find use in a wide variety of contexts, including any context in which it is desirable to monitor for hemodynamically significant heart rhythm disturbances in an individual.

Cardiac arrest leading to sudden cardiac death (SCD) is a major cause of worldwide mortality. Early rescue (within 2-5 minutes) from lethal heart rhythms by emergency medical systems (EMS) paramedics is the most important and critical determinant of survival from otherwise fatal cardiac arrests. The large majority of cardiac arrests are unwitnessed and therefore cannot be rescued because EMS is not alerted, while many witnessed cardiac arrest victims suffer a delay to EMS alert, preventing timely rescue. Even if an individual is resuscitated from the initial arrest, prolonged time to EMS activation can lead to catastrophic and debilitating consequences, such as anoxic brain injury, kidney failure, and damage to other vital organs. In addition, delayed EMS activation may lead to costly ICU stays and often unfortunately death.

The methods, computer-readable media and computing devices of the present disclosure utilize unconventional aspects of PPG signals for accurate detection of hemodynamically significant heart rhythm disturbances and, in certain embodiments, allow for immediate and early detection of hemodynamically significant heart rhythm disturbances by a wearable device such as smartwatch, direct and immediate alert and communication to 911 and EMS via paired cellular phone or built-in cellular modem to direct paramedics to cardiac arrest victims at their precise location communicated by GPS (or cell phone triangulation or WiFi) for timely resuscitation and improved survival from cardiac arrest. The methods, computer-readable media and computing devices of the present disclosure also provide for reduced morbidity and a substantial reduction in healthcare expenditures.

The following examples are offered by way of illustration and not by way of limitation.

EXPERIMENTAL

Figure 5:
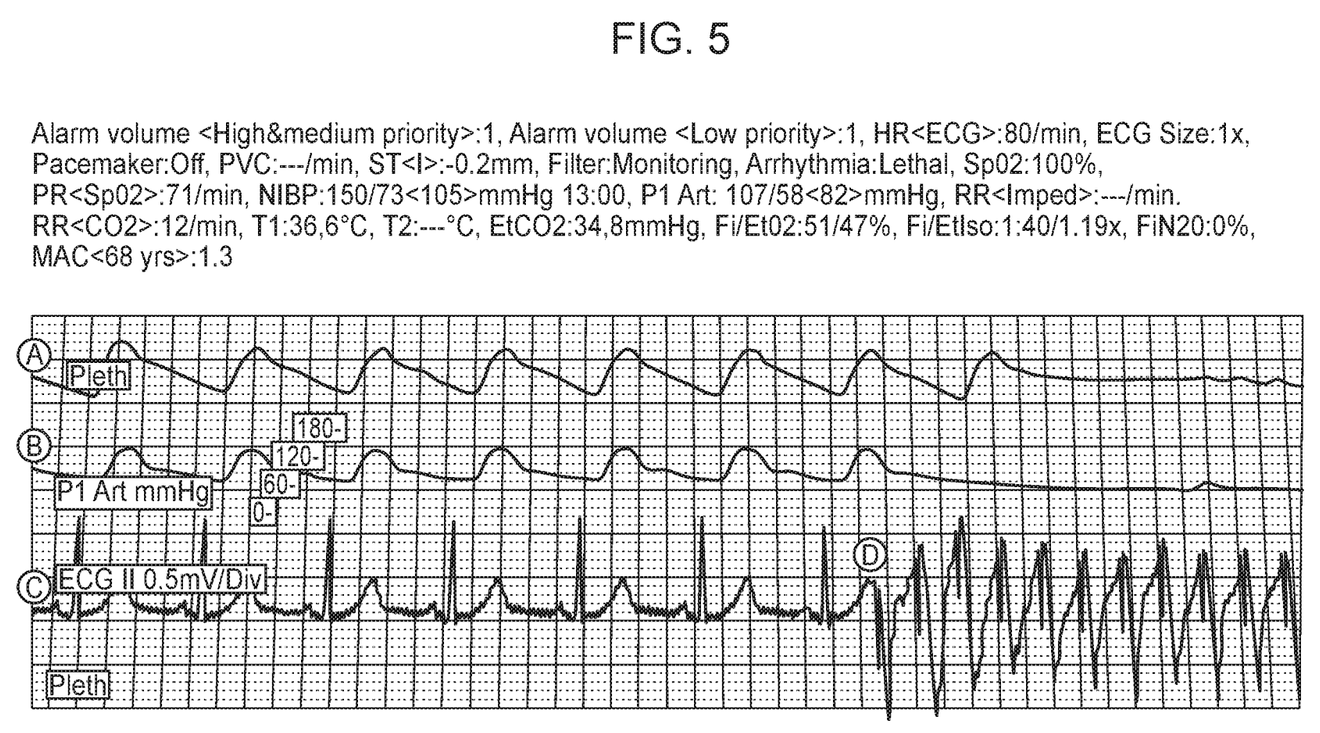
FIG. 5 shows PPG, invasive blood pressure, and ECG rhythm tracings prior to a during rapid ventricular pacing.

Example 1—Correlation Between Simultaneous PPG, Invasive Blood Pressure, and ECG Rhythm Tracings During Rapid Ventricular Pacing Simultaneous rhythm traces from PPG, invasive blood pressure monitoring, and ECG were obtained from an anesthetized individual during a cardiac electrophysiology procedure. As shown in FIG. 5, excellent correlation between simultaneous PPG (A), invasive blood pressure (B), and ECG rhythm (C) tracings from anesthesia monitor during normal sinus rhythm (left) and rapid ventricular pacing (right, D) was observed. Rapid ventricular pacing simulates rapid ventricular tachycardia, a common heart rhythm disturbance of cardiac arrest.

Example 2—Detection and Early Alert of Cardiac Arrest for Timely Resuscitation by Emergency Responders Via a Wearable Device An individual develops ventricular fibrillation while wearing a smartwatch or fitness tracker with an application installed thereon for—inter alia—obtaining baseline PPG data and monitoring for hemodynamically significant heart rhythm disturbances. The PPG (detecting a threshold decreased amplitude and/or slope in the initial positive deflection of the waveform), temperature (to confirm the device is being worn by the individual) and accelerometer (to confirm lack of substantial movement) data obtained by the smartwatch or fitness tracker is used to meet criteria to detect cardiac arrest. The device then alarms, providing an opportunity for a "false positive" result to be aborted by the individual. In the absence of deactivation of the alarm, the device uses GPS and/or cell-phone triangulation to determine the location of the individual. The device then communicates the location of the cardiac arrest individual to emergency medical services, including tracings (with timestamps) of the event. The individual's medical history, including medicine and allergies, are also communicated to EMS. EMS arrives and successfully resuscitates the individual, preventing an otherwise fatal event and mitigating the risk of brain and/or other bodily injury.

Example 3—Detection of a Hemodynamically Significant Heart Rhythm Disturbance by PPG Using a Smartwatch Loaded with a Mobile Application for Monitoring for Hemodynamically Significant Heart Rhythm Disturbances In this example, the heart rhythms of a human patient undergoing defibrillator implantation surgery were monitored by PPG using a smartwatch having a PPG light-based sensor to detect the frequency and intensity of light derived from the pulse. The smartwatch was loaded with a mobile application for monitoring for hemodynamically significant heart rhythm disturbances in accordance with aspects of the methods, computer-readable media and devices of the present disclosure.

Figure 6:
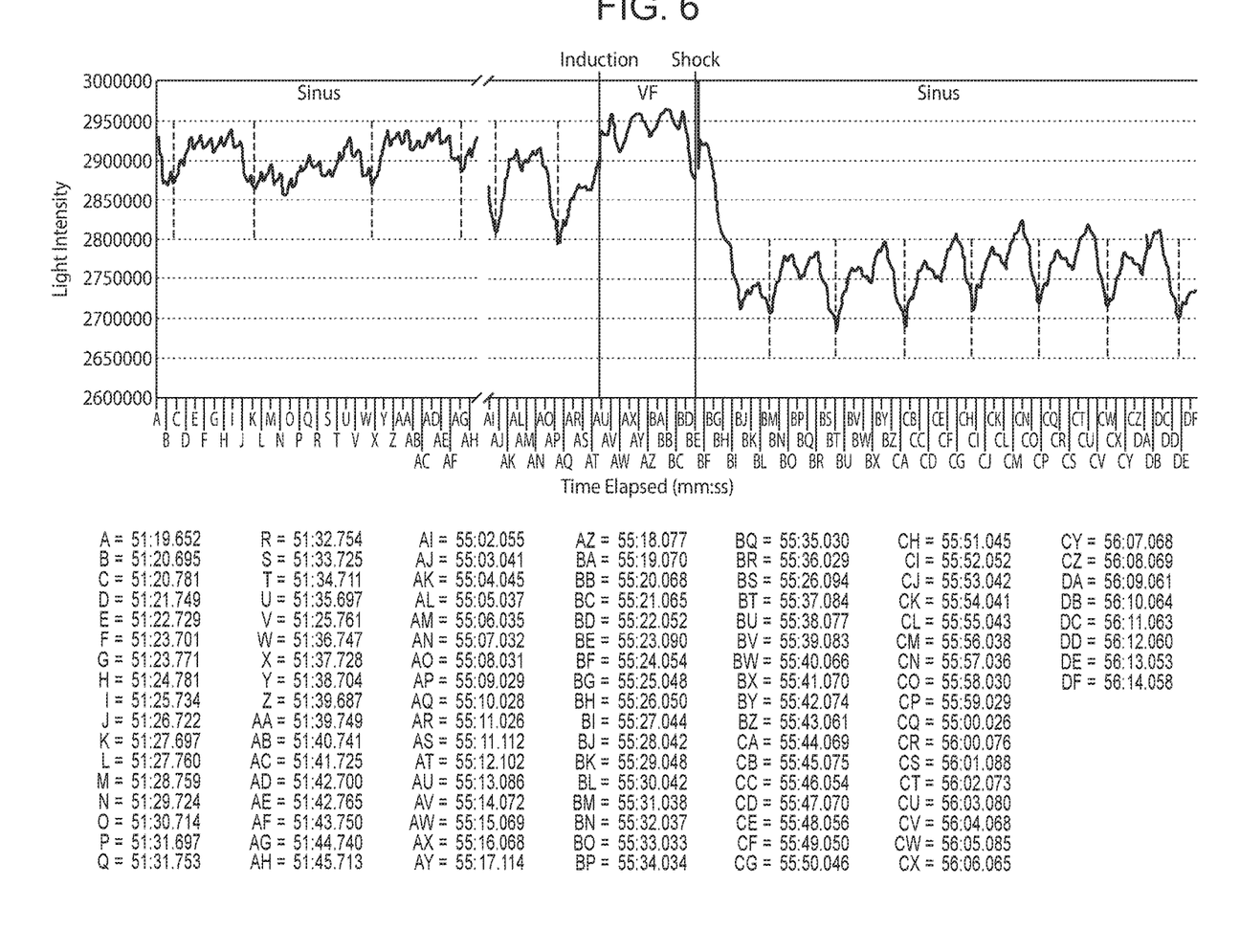
FIG. 6 shows a PPG trace recorded by a smartwatch loaded with a mobile application from a human patient in normal rhythm, during ventricular fibrillation (cardiac arrest), and after shock, return to normal rhythm.

Ventricular fibrillation (VF) was induced in the patient, followed by a shock to return the patient to normal rhythm. VF is a hemodynamically significant heart rhythm disturbance that occurs in the setting of sudden death or cardiac arrest. Shown in FIG. 6 is the PPG trace of the individual prior to induction of VF, during VF (post-induction), and subsequent to VF (post-shock). As is apparent from FIG. 6, the PPG waveforms during VF exhibit reduced amplitude and decreased slope in the initial positive deflection compared to the normal rhythms pre- and post-VF. The signals were processed in this experiment such that more light intensity reflects reduced blood flow (and therefore sudden inflow of blood as expected). The vertical dashed lines in FIG. 6 point out the clear, repetitive, sinus rhythm tracing, where the initial part of each beat has a sharp upstroke (steep slope). During VF, it is clear that the regularity and steep upslope are no longer present—as well as greater light intensity. Post-shock, the regular pattern of normal sinus rhythm returned, demarcated by the reliable sharp upstrokes (steep slopes), which were not observed during VF. This example demonstrates the utility of a wearable device for PPG-based monitoring for hemodynamically significant heart rhythm disturbances in an individual.

Notwithstanding the appended claims, the disclosure is also defined by the following embodiments:

1. A method of monitoring for a hemodynamically significant heart rhythm disturbance in an individual, comprising:
   (a) obtaining baseline photoplethysmography (PPG) data from an individual during normal sinus rhythm;
   (b) obtaining PPG signals from the individual during a monitoring period;
   (c) comparing the PPG signals obtained during the monitoring period to the baseline PPG data;
   (d) producing an output when a hemodynamically significant heart rhythm disturbance is detected, wherein detecting a hemodynamically significant heart rhythm disturbance comprises:
      detecting a threshold reduction in PPG amplitude in the PPG signals obtained during the monitoring period compared to the baseline PPG data for a selected period of time;
      detecting a threshold decreased slope in the initial positive deflection in PPG signals obtained during the monitoring period compared to the baseline PPG data for a selected number of consecutive beats; or both.

2. The method according to Embodiment 1, comprising updating the baseline PPG data continuously or at a selected interval.

3. The method according to Embodiment 1 or Embodiment 2, wherein the threshold reduction in PPG amplitude is 20% or greater.

4. The method according to any one of Embodiments 1 to 3, wherein the selected period of time is 3 or more seconds.

5. The method according to any one of Embodiments 1 to 4, wherein the threshold decreased slope in the initial positive deflection is 10% or greater.

6. The method according to any one of Embodiments 1 to 5, wherein the selected number of consecutive beats is 3 or more consecutive beats.

7. The method according to any one of Embodiments 1 to 6, wherein detecting a hemodynamically significant heart rhythm disturbance further comprises photoplethysmographically detecting a hemodynamically significant heart rate for a selected period of time.

8. The method according to Embodiment 7, wherein the hemodynamically significant heart rate is 30 beats per minute (bpm) or slower.

9. The method according to Embodiment 7, wherein the hemodynamically significant heart rate is greater than 220 bpm minus the age in years of the individual.

10. The method according to any one of Embodiments 7 to 9, wherein the selected period of time for the hemodynamically significant heart rate is 3 or more seconds.

11. The method according to any one of Embodiments 1 to 10, wherein detecting a hemodynamically significant heart rhythm disturbance further comprises detecting a threshold reduction or absence of movement of the individual.

12. The method according to any one of Embodiments 1 to 11, wherein detecting a hemodynamically significant heart rhythm disturbance further comprises detecting a threshold reduction in body temperature of the individual.

13. The method according to any one of Embodiments 1 to 12, wherein producing an output comprises producing an alert to the individual, a bystander, or both, that a hemodynamically significant heart rhythm disturbance has been detected.

14. The method according to Embodiment 13, wherein the alert is selected from the group consisting of: a visual alert, an auditory alert, a vibratory alert, and any combination thereof.

15. The method according to Embodiment 14, wherein the alert comprises an auditory alert.

16. The method according to Embodiment 15, wherein the auditory alert comprises a voice alert.

17. The method according to any one of Embodiments 13 to 16, wherein producing an alert comprises requesting a response from the individual.

18. The method according to Embodiment 17, comprising deactivating the alert when the individual responds to the alert.

19. The method according to any one of Embodiments 1 to 18, wherein producing an output comprises producing an alert to a first responder.

20. The method according to Embodiment 19, wherein an alert to a first responder is produced only in the absence of a response from the individual to an alert to the individual.

21. The method according to Embodiment 19 or Embodiment 20, wherein producing an alert to a first responder comprises providing the location of the individual to the first responder.

22. The method according to any one of Embodiments 19 to 21, wherein the first responder is selected from the group consisting of: an emergency medical service (EMS), the police, a fire department, and any combination thereof.

23. The method according to any one of Embodiments 1 to 22, wherein the individual does not have a history of experiencing a hemodynamically significant heart rhythm disturbance.

24. The method according to any one of Embodiments 1 to 22, wherein the individual has a history of experiencing a hemodynamically significant heart rhythm disturbance.

25. The method according to Embodiment 23 or Embodiment 24, wherein the hemodynamically significant heart rhythm disturbance is selected from the group consisting of: ventricular tachycardia (VT), ventricular fibrillation (VF), bradycardia, asystole, and any combination thereof.

26. The method according to any one of Embodiments 1 to 25, wherein the steps of the method are performed using a wearable device.

27. The method according to Embodiment 26, wherein the wearable device is a wrist-wearable device.

28. A non-transitory computer-readable medium storing instructions that, when executed by a computing device, cause the computing device to:
(a) obtain baseline photoplethysmography (PPG) data from an individual during normal sinus rhythm;
(b) obtain PPG signals from the individual during a monitoring period;
(c) compare the PPG signals obtained during the monitoring period to the baseline PPG data;
(d) produce an output when a hemodynamically significant heart rhythm disturbance is detected, wherein detecting a hemodynamically significant heart rhythm disturbance comprises:
detecting a threshold reduction in PPG amplitude in the PPG signals obtained during the monitoring period compared to the baseline PPG data for a selected period of time;
detecting a threshold decreased slope in the initial positive deflection in PPG signals obtained during the monitoring period compared to the baseline PPG data for a selected number of consecutive beats; or both.

29. The non-transitory computer-readable medium of Embodiment 28, wherein the instructions, when executed by a computing device, further cause the computing device to update the baseline PPG data continuously or at a selected interval.

30. The non-transitory computer-readable medium of Embodiment 28 or Embodiment 29, wherein the threshold reduction in PPG amplitude is 20% or greater.

31. The non-transitory computer-readable medium of any one of Embodiments 28 to 30, wherein the selected period of time is 3 or more seconds.

32. The non-transitory computer-readable medium of any one of Embodiments 28 to 31, wherein the threshold decreased slope in the initial positive deflection is 10% or greater.

33. The non-transitory computer-readable medium of any one of Embodiments 28 to 32, wherein the selected number of consecutive beats is 3 or more consecutive beats.

34. The non-transitory computer-readable medium of any one of Embodiments 28 to 33, wherein detecting a hemodynamically significant heart rhythm disturbance further comprises photoplethysmographically detecting a hemodynamically significant heart rate for a selected period of time.

35. The non-transitory computer-readable medium of Embodiment 34, wherein the hemodynamically significant heart rate is 30 beats per minute (bpm) or slower.

36. The non-transitory computer-readable medium of Embodiment 34, wherein the hemodynamically significant heart rate is greater than 220 bpm minus the age in years of the individual.

37. The non-transitory computer-readable medium of any one of Embodiments 34 to 36, wherein the selected period of time for the hemodynamically significant heart rate is 3 or more seconds.

38. The non-transitory computer-readable medium of any one of Embodiments 28 to 37, wherein detecting a hemodynamically significant heart rhythm disturbance further comprises detecting a threshold reduction or absence of movement of the individual.

39. The non-transitory computer-readable medium of any one of Embodiments 28 to 38, wherein detecting a hemodynamically significant heart rhythm disturbance further comprises detecting a threshold reduction in body temperature of the individual.

40. The non-transitory computer-readable medium of any one of Embodiments 28 to 39, wherein the output comprises an alert to the individual, a bystander, or both, that a hemodynamically significant heart rhythm disturbance has been detected.

41. The non-transitory computer-readable medium of Embodiment 40, wherein the alert is selected from the group consisting of: a visual alert, an auditory alert, a vibratory alert, and any combination thereof.

42. The non-transitory computer-readable medium of Embodiment 41, wherein the alert comprises an auditory alert.

43. The non-transitory computer-readable medium of Embodiment 42, wherein the auditory alert comprises a voice alert.

44. The non-transitory computer-readable medium of any one of Embodiments 40 to 43, wherein producing an alert comprises requesting a response from the individual.

45. The non-transitory computer-readable medium of Embodiment 44, wherein the instructions, when executed by a computing device, further cause the computing device to deactivate the alert when the individual responds to the alert.

46. The non-transitory computer-readable medium of any one of Embodiments 28 to 45, wherein the output comprises an alert to a first responder.

47. The non-transitory computer-readable medium of Embodiment 46, wherein the instructions, when executed by a computing device, further cause the computing device to produce an alert to a first responder only in the absence of a response from the individual to an alert to the individual.

48. The non-transitory computer-readable medium of Embodiment 46 or Embodiment 47, wherein the alert to a first responder comprises providing the location of the individual to the first responder.

49. The non-transitory computer-readable medium of any one of Embodiments 46 to 48, wherein the first responder is selected from the group consisting of: an emergency medical service (EMS), the police, a fire department, and any combination thereof.

50. The non-transitory computer-readable medium of any one of Embodiments 28 to 49, wherein the hemodynamically significant heart rhythm disturbance is selected from the group consisting of: ventricular tachycardia (VT), ventricular fibrillation (VF), bradycardia, asystole, and any combination thereof.

51. The non-transitory computer-readable medium of any one of Embodiments 28 to 50, wherein the instructions are present on a server.

52. The non-transitory computer-readable medium of Embodiment 51, wherein the instructions are downloadable from the server to a computing device.

53. A computing device for monitoring for a hemodynamically significant heart rhythm disturbance in an individual, comprising:
a photoplethysmographic (PPG) sensor;
a processing unit; and
a non-transitory computer-readable medium comprising instructions that, when executed by the computing device, cause the computing device to:
(a) using the PPG sensor, obtain baseline photoplethysmography (PPG) data from an individual during normal sinus rhythm;
(b) using the PPG sensor, obtain PPG signals from the individual during a monitoring period;

(c) compare the PPG signals obtained during the monitoring period to the baseline PPG data;
(d) produce an output when a hemodynamically significant heart rhythm disturbance is detected, wherein detecting a hemodynamically significant heart rhythm disturbance comprises:
  detecting a threshold reduction in PPG amplitude in the PPG signals obtained during the monitoring period compared to the baseline PPG data for a selected period of time;
  detecting a threshold decreased slope in the initial positive deflection in PPG signals obtained during the monitoring period compared to the baseline PPG data for a selected number of consecutive beats; or
  both.

54. The computing device of Embodiment 53, wherein the computing device is selected from the group consisting of: a desktop computer, a laptop computer, a tablet computer, a smartphone, and a wearable device.

55. The computing device of Embodiment 53, wherein the computing device comprises a wearable device.

56. The computing device of Embodiment 55, wherein the wearable device is adapted to obtain PPG signals from the individual's forehead, ear, upper arm, wrist, leg, torso, or a combination thereof.

57. The computing device of Embodiment 56, wherein the wearable device is a wrist-wearable device.

58. The computing device of Embodiment 57, wherein the wrist-wearable device is a smartwatch.

59. The computing device of any one of Embodiments 53 to 58, wherein the instructions, when executed by the computing device, further cause the computing device to update the baseline PPG data continuously or at a selected interval.

60. The computing device of any one of Embodiments 53 to 59, wherein the threshold reduction in PPG amplitude is 20% or greater.

61. The computing device of any one of Embodiments 53 to 60, wherein the selected period of time is 3 or more seconds.

62. The computing device of any one of Embodiments 53 to 61, wherein the threshold decreased slope in the initial positive deflection is 10% or greater.

63. The computing device of any one of Embodiments 53 to 62, wherein the selected number of consecutive beats is 3 or more consecutive beats.

64. The computing device of any one of Embodiments 53 to 63, wherein detecting a hemodynamically significant heart rhythm disturbance further comprises photoplethysmographically detecting a hemodynamically significant heart rate for a selected period of time.

65. The computing device of Embodiment 64, wherein the hemodynamically significant heart rate is 30 beats per minute (bpm) or slower.

66. The computing device of Embodiment 64, wherein the hemodynamically significant heart rate is greater than 220 bpm minus the age in years of the individual.

67. The computing device of any one of Embodiments 64 to 66, wherein the selected period of time for the hemodynamically significant heart rate is 3 or more seconds.

68. The computing device of any one of Embodiments 53 to 67, wherein detecting a hemodynamically significant heart rhythm disturbance further comprises detecting a threshold reduction or absence of movement of the individual.

69. The computing device of any one of Embodiments 53 to 68, wherein detecting a hemodynamically significant heart rhythm disturbance further comprises detecting a threshold reduction in body temperature of the individual.

70. The computing device of any one of Embodiments 53 to 69, wherein the output comprises an alert to the individual, a bystander, or both, that a hemodynamically significant heart rhythm disturbance has been detected.

71. The computing device of Embodiment 70, wherein the alert is selected from the group consisting of: a visual alert, an auditory alert, a vibratory alert, and any combination thereof.

72. The computing device of Embodiment 71, wherein the alert comprises an auditory alert.

73. The computing device of Embodiment 72, wherein the auditory alert comprises a voice alert.

74. The computing device of any one of Embodiments 70 to 73, wherein producing an alert comprises requesting a response from the individual.

75. The computing device of Embodiment 74, wherein the instructions, when executed by a computing device, further cause the computing device to deactivate the alert when the individual responds to the alert.

76. The computing device of any one of Embodiments 53 to 45, wherein the output comprises an alert to a first responder.

77. The computing device of Embodiment 76, wherein the instructions, when executed by a computing device, further cause the computing device to produce an alert to a first responder only in the absence of a response from the individual to an alert to the individual.

78. The computing device of Embodiment 76 or Embodiment 77, wherein the alert to a first responder comprises providing the location of the individual to the first responder.

79. The computing device of any one of Embodiments 76 to 78, wherein the first responder is selected from the group consisting of: an emergency medical service (EMS), the police, a fire department, and any combination thereof.

80. The computing device of any one of Embodiments 53 to 79, wherein the hemodynamically significant heart rhythm disturbance is selected from the group consisting of: ventricular tachycardia (VT), ventricular fibrillation (VF), bradycardia, asystole, and any combination thereof.

81. The computing device of any one of Embodiments 53 to 80, wherein the instructions are present on a server.

82. The computing device of Embodiment 81, wherein the instructions are downloadable from the server to a computing device.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A method of monitoring for a hemodynamically significant heart rhythm disturbance in an individual, comprising:
    (a) obtaining baseline photoplethysmography (PPG) data from an individual during normal sinus rhythm;
    (b) obtaining PPG signals from the individual during a monitoring period;
    (c) comparing the PPG signals obtained during the monitoring period to the baseline PPG data;
    (d) producing an output when a hemodynamically significant heart rhythm disturbance is detected, wherein detecting a hemodynamically significant heart rhythm disturbance comprises:
        detecting a threshold reduction in PPG amplitude in the PPG signals obtained during the monitoring period compared to the baseline PPG data for a selected period of time;
        detecting a threshold decreased slope in the initial positive deflection in PPG signals obtained during the monitoring period compared to the baseline PPG data for a selected number of consecutive beats; or both.

2. The method according to claim 1, comprising updating the baseline PPG data continuously or at a selected interval.

3. The method according to claim 1, wherein the threshold reduction in PPG amplitude is 20% or greater.

4. The method according to claim 1, wherein the selected period of time is 3 or more seconds.

5. The method according to claim 1, wherein the threshold decreased slope in the initial positive deflection is 10% or greater.

6. The method according to claim 1, wherein the selected number of consecutive beats is 3 or more consecutive beats.

7. The method according to claim 1, wherein detecting a hemodynamically significant heart rhythm disturbance further comprises photoplethysmographically detecting a hemodynamically significant heart rate for a selected period of time.

8. The method according to claim 1, wherein detecting a hemodynamically significant heart rhythm disturbance further comprises detecting a threshold reduction or absence of movement of the individual, detecting a threshold reduction in body temperature of the individual, or both.

9. The method according to claim 1, wherein producing an output comprises producing an alert to the individual, a bystander, or both, that a hemodynamically significant heart rhythm disturbance has been detected.

10. The method according to claim 1, wherein producing an output comprises producing an alert to a first responder.

11. The method according to claim 10, wherein an alert to a first responder is produced only in the absence of a response from the individual to an alert to the individual.

12. The method according to claim 11, wherein producing an alert to a first responder comprises providing the location of the individual to the first responder.

13. The method according to claim 1, wherein the steps of the method are performed using a wearable device.

14. The method according to claim 13, wherein the wearable device is a wrist-wearable device.

15. A non-transitory computer-readable medium storing instructions that, when executed by a computing device, cause the computing device to:
    (a) obtain baseline photoplethysmography (PPG) data from an individual during normal sinus rhythm;
    (b) obtain PPG signals from the individual during a monitoring period;
    (c) compare the PPG signals obtained during the monitoring period to the baseline PPG data;
    (d) produce an output when a hemodynamically significant heart rhythm disturbance is detected, wherein detecting a hemodynamically significant heart rhythm disturbance comprises:
        detecting a threshold reduction in PPG amplitude in the PPG signals obtained during the monitoring period compared to the baseline PPG data for a selected period of time;
        detecting a threshold decreased slope in the initial positive deflection in PPG signals obtained during the monitoring period compared to the baseline PPG data for a selected number of consecutive beats; or both.

16. The non-transitory computer-readable medium of claim 15, wherein the instructions, when executed by a computing device, further cause the computing device to update the baseline PPG data continuously or at a selected interval.

17. The non-transitory computer-readable medium of claim 15, wherein the threshold reduction in PPG amplitude is 20% or greater.

18. A computing device for monitoring for a hemodynamically significant heart rhythm disturbance in an individual, comprising:
    a photoplethysmographic (PPG) sensor;
    a processing unit; and
    a non-transitory computer-readable medium comprising instructions that, when executed by the computing device, cause the computing device to:
        (a) using the PPG sensor, obtain baseline photoplethysmography (PPG) data from an individual during normal sinus rhythm;
        (b) using the PPG sensor, obtain PPG signals from the individual during a monitoring period;
        (c) compare the PPG signals obtained during the monitoring period to the baseline PPG data;
        (d) produce an output when a hemodynamically significant heart rhythm disturbance is detected, wherein detecting a hemodynamically significant heart rhythm disturbance comprises:
            detecting a threshold reduction in PPG amplitude in the PPG signals obtained during the monitoring period compared to the baseline PPG data for a selected period of time;
            detecting a threshold decreased slope in the initial positive deflection in PPG signals obtained during the monitoring period compared to the baseline PPG data for a selected number of consecutive beats; or both.

19. The computing device of claim 18, wherein the computing device comprises a wearable device.

20. The computing device of claim 19, wherein the wearable device is a wrist-wearable device.

* * * * *